United States Patent [19]

Knops et al.

[11] 4,291,046
[45] * Sep. 22, 1981

[54] PREPARATION OF NOVEL FUNGICIDALLY ACTIVE SPIRO DERIVATIVES OF 3-(3,5-DIHALOGENOPHENYL)-OXAZOLI-DINE-2-THION-4-ONES

[75] Inventors: Hans-Joachim Knops, Wuppertal; Hans-Georg Heine, Krefeld; Wilfried Draber, Wuppertal; Wilhelm Brandes, Leichlingen, all of Fed. Rep. of Germany

[73] Assignee: Bayer Aktiengesellschaft, Leverkusen, Fed. Rep. of Germany

[*] Notice: The portion of the term of this patent subsequent to Apr. 29, 1997, has been disclaimed.

[21] Appl. No.: 117,134

[22] Filed: Jan. 30, 1980

[30] Foreign Application Priority Data

Feb. 15, 1979 [DE] Fed. Rep. of Germany ....... 2905780

[51] Int. Cl.³ .................. A01N 43/76; C07D 263/04
[52] U.S. Cl. ..................................... 424/272; 548/216
[58] Field of Search ........................ 548/216; 424/272

[56] References Cited

U.S. PATENT DOCUMENTS 4,200,643  4/1980  Knops et al. ..................... 548/216

*Primary Examiner*—Anton H. Sutto
*Attorney, Agent, or Firm*—Sprung, Felfe, Horn, Lynch & Kramer

[57] ABSTRACT

Fungicidally active novel spiro derivatives of 3-(3,5-dihalogenophenyl)-oxazolidine-2-thion-4-ones of the formula

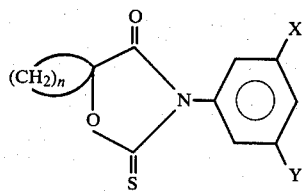

in which X and Y each independently is halogen, and
n is 2 or 3, are produced by reacting an α-hydroxy-cycloalkylcarboxylic acid or acid ester of the formula

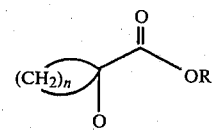

in which
R is hydrogen or alkyl with 1 to 4 carbon atoms,
(a) with an isothiocyanate of the formula

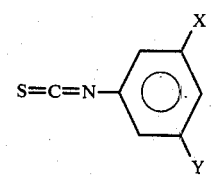

or
(b) with an aniline of the formula

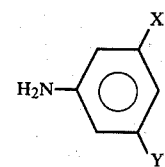

in the presence of a diluent, and then cyclizing the α-hydroxycycloalkyl-carboxylic acid amide formed of the formula

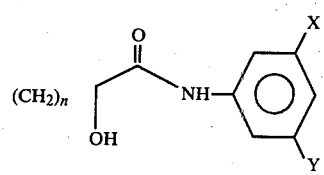

15 Claims, No Drawings

PREPARATION OF NOVEL FUNGICIDALLY ACTIVE SPIRO DERIVATIVES OF 3-(3,5-DIHALOGENOPHENYL)-OXAZOLIDINE-2-THION-4-ONES

The present invention relates to certain new spiro derivatives of 3-(3,5-dihalogenophenyl)-oxazolidine-2-thion-4-ones, to a process for their preparation and to their use as fungicides.

It has already been disclosed that certain thiuram disulphides, for example tetramethyl-thiuram disulphide, have good fungicidal properties (see U.S. Pat. No. 1,972,961). However, in certain fields of indication, the action of this class of substances is not always completely satisfactory, especially when small amounts of low concentration are used.

The present invention now provides, as new compounds, the spiro derivatives of 3-(3,5-dihalogenophenyl)-oxazolidine-2-thion-4-ones of the general formula

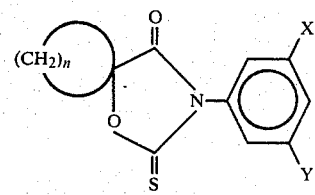

(I)

in which
X and Y are identical or different and represent halogen (in particular, fluorine, chlorine, bromine or iodine) and
n represents the integer 2 or 3.

Those compounds of the formula (I) in which X and Y represent chlorine are particularly preferred.

Surprisingly, the spiro derivatives, according to the invention, of 3-(3,5-dihalogenophenyl)-oxazolidine-2-thion-4-ones have a considerably higher fungicidal action, in particular against species of Botrytis, than the compound tetramethyl-thiaram disulphide, which is known from the state of the art and is recognized as a good agent of the same type of action. The active compounds according to the invention thus represent an enrichment of the art.

The invention also provides a process for the preparation of a spiro derivative of a 3-(3,5-dihalogenophenyl)-oxazolidine-2-thion-4-one of the formula (I) in which an α-hydroxy-cycloalkylcarboxylic acid or acid ester of the general formula

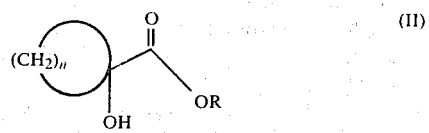

(II)

in which
R represents hydrogen or alkyl with 1 to 4 carbon atoms and
n has the meaning indicated above,
(a) is reacted with an isothiocyanate of the general formula

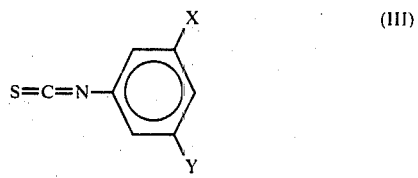

(III)

in which
X and Y have the meanings indicated above, if appropriate in the presence of a base and in the presence of a diluent, or
(b) is reacted with an aniline of the general formula

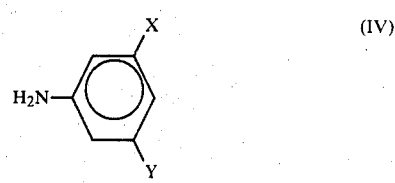

(IV)

in which
X and Y have the meanings indicated above, in the presence of a diluent, and the α-hydroxy-cycloalkylcarboxylic acid amide formed, of the general formula

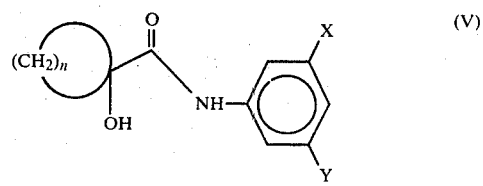

(V)

in which
X, Y and n have the meanings indicated above, is cyclized with thiophosgene in the presence of a base.

If α-hydroxycyclopropanecarboxylic acid and 3,5-dichlorophenyl isothiocyanate are used as starting materials in process variant (a), the course of the reaction can be represented by the following equation:

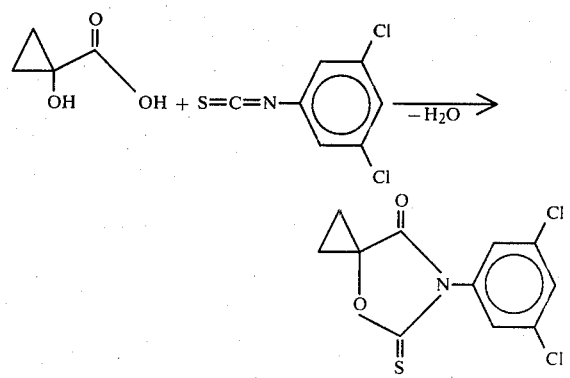

If α-hydroxybutanecarboxylic acid ethyl ester and 3,5-dibromophenyl isothiocyanate are used as starting materials in process variant (a), the course of the reaction can be represented by the following equation:

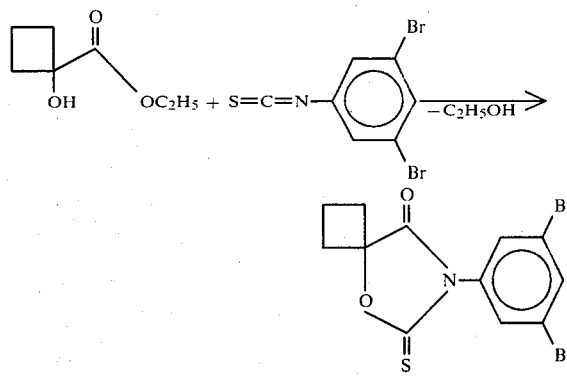

If α-hydroxy-cyclopropanecarboxylic acid, 3,5-dichloroaniline and thiophosgene are used as starting materials in process variant (b), the course of the reaction can be represented by the following equations:

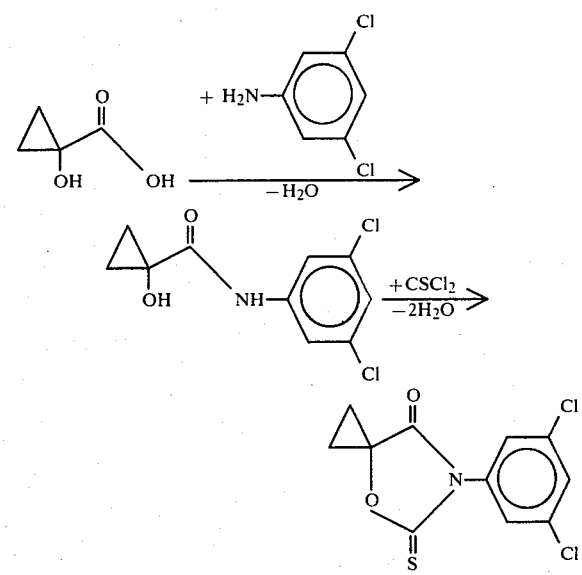

The formula (II) provides a general definition of the α-hydroxy-cycloalkylcaboxylic acids and acid esters to be used as starting substances. In this formula, R preferably represents straight-chain or branched alkyl with 1 to 4 carbon atoms, especially methyl or ethyl. The index n preferably represents the integer 2 or 3.

The starting materials of the formula (II) are known (see Liebigs Ann. Chem. 1976, 463 and Chem. Ber. 55, 2738 (1922)). Examples which may be mentioned are α-hydroxycyclopropanecarboxylic acid, α-hydroxycyclopropanecarboxylic acid methyl ester and ethyl ester, α-hydroxy-cyclobutanecarboxylic acid methyl ester and ethyl ester and α-hydroxycyclobutanecarboxylic acid.

α-Hydroxy-cyclopropanecarboxylic acid can be prepared, for example, by a procedure in which 1,2-bis-(trimethylsiloxy)-1-cyclobutane is first prepared by acyloin condensation of a succinic acid ester in the presence of trimethylchlorosilane and the resulting compound is then brominated, 1-hydroxycyclopropanecarboxylic acid being obtained by ring contraction by the route via 1,2-cyclobutane-dione. 1-Hydroxy-cyclobutanecarboxylic acid can be prepared, for example, by a process in which cyclobutanecarboxylic acid is brominated and the resulting 1-bromo compound is then treated with an aqueous potassium carbonate solution.

The formula (III) provides a general definition of the isothiocyanates, and the formula (IV) a general definition of the anilines, also to be used as starting materials. In these formulae, X and Y are identical or different and preferably represent fluorine, chlorine, bromine or iodine.

The starting materials of the formulae (III) and (IV) are generally known compounds of organic chemistry.

Preferred diluents for the reaction in process variant (a) are inert organic solvents. These include, as preferences, aromatic hydrocarbons, for example, benzene, toluene, xylene or 1,2-dichlorobenzene, or halogenated hydrocarbons, for example methylene chloride, chloroform or carbon tetrachloride.

If the reaction in process variant (a) is carried out in the presence of a base, it is possible to employ any of the organic and inorganic bases which can customarily be used. These bases include, as preferences, tertiary amines, for example triethylamine or pyridine, and alcoholates, for example, potassium tert.-butylate or sodium tert.-butylate.

The reaction temperatures can be varied within a substantial range in process variant (a). In general, the reaction is carried out at about 20° to 100° C., preferably at the boiling point of the particular solvent.

Equimolar amounts of the reactants are preferably used in carrying out process variant (a). If a base is used, this is employed in an equimolar amount if an α-hydroxycycloalkanecarboxylic acid is used as the starting material, and only in a catalytic amount if an α-hydroxycycloalkanecarboxylic acid ester is employed. To isolate the compound of the formula (I), the solvent is distilled off and the residue is worked up.

Preferred diluents for the reaction in process variant (b) are inert organic solvents. These include, as preferences, the solvents already mentioned in the case of process variant (a).

Preferred bases for the reaction in process variant (b), are those reagents which have already been mentioned in the case of variant (a).

The reaction temperatures can be varied within a substantial range in process variant (b). In general, the reaction is carried out at about 20° to 100° C., preferably at the boiling point of the solvent used.

Equimolar amounts of the reactants are preferably used in carrying out process variant (b). The α-hydroxy-cycloalkylcarboxylic acid amide of the formula (V) formed as the intermediate product can be reacted directly, without isolation. To isolate the compound of the formula (I), the solvent is distilled off and the residue is worked up by customary methods.

The compounds according to the invention exhibit a powerful microbicidal action and can be employed in practice for combating undesired micro-organisms. The active compounds are suitable for use as plant protection agents.

Fungicidal agents in plant protection are employed for combating Plasmodiophoromycetes, Oomycetes, Ohytridiomycetes, Zygomycetes, Ascomycetes, Basidiomycetes anrd Deuteromycetes.

The good toleration, by plants, of the active compounds, at the concentration required for combating plant diseases, permits treatment of above-ground parts of plants, of vegetative propagation stock and seeds, and of the soil.

As plant protection agents, the active compounds according to the invention can be used with particularly good success for combating Botrytis species, such as against the causative organisms of grey mold on strawberries or grapes (*Botrytis cinerea*).

The active compounds can be converted into the customary formulations, such as solutions, emulsions, powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations, or in the various use forms, as a mixture with other active compounds, such as fungicides, bactericides, insecticides, acaricides, nematicides, herbicides, bird repellants, growth factors, plant nutrient and agents for improving soil structure.

The active compounds can be used as such or in the form of their formulations or the use forms prepared therefrom by further dilution, such as ready-to-use solutions, emulsions, suspensions, powders, pastes and granules. They may be used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

Especially in the treatment of part of plants, the active compound concentrations in the use forms can be varied within a substantial range. They are, in general, from 1 to 0.0001% by weight, preferably from 0.5 to 0.001%.

In the treatment of seed, amounts of active compound of 0.001 to 50 g, preferably 0.01 to 10 g, are generally required per kilogram of seed.

For the treatment of soil, active compound concentrations of 0.00001 to 0.1% by weight, preferably 0.0001 to 0.02%, are required at the place of action.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

The preparation of the novel compounds is shown in the following illustrative example:

EXAMPLE 1

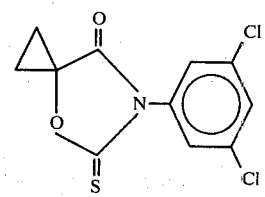
(1)

5.1 g (0.05 mol) of α-hydroxycyclopropanecarboxylic acid and 5.05 g of triethylamine were dissolved in 200 ml of o-dichlorobenzene at about 100° C. A solution of 10.2 g (0.05 mol) of 3,5-dichlorophenyl isothiocyanate in 50 ml of o-dichlorobenzene was added dropwise and the mixture was then heated under reflux for 3 hours, using a water separator. The mixture was allowed to cool and was concentrated by distilling off the solvent in vacuo. 100 ml of hot ethanol were added to the still warm residue and the components were mixed thoroughly. During cooling, white crystals separated out, and were filtered off and recrystallized from ethanol.

6 g (45% of theory) of 1-oxa-3-aza-spiro[4,2]-hepta-3-(3,5-dichlorophenyl)-2-thion-4-one of melting point 154° C. were obtained.

The following compounds of the general formula (I) can be prepared similarly:

(I)

| Compound | X | Y | n |
|---|---|---|---|
| 2 | Cl | Cl | 3 |
| 3 | Br | Br | 2 |
| 4 | Br | Br | 3 |
| 5 | I | I | 2 |
| 6 | Cl | Br | 2 |
| 7 | Cl | Br | 3 |

The fungicidal activity of the compounds of this invention is illustrated by the following example.

EXAMPLE 2

Botrytis test (beans)/protective

Solvent: 4.7 parts by weight of acetone
Dispersing agent: 0.3 part by weight of alkylaryl polyglycol ether
Water: 95.0 parts by weight The amount of active compound required to give the desired concentration of active compound in the spray liquid was mixed with the stated amount of the solvent and the concentrate was diluted with the stated amount of water which contained the stated additive.

*Phaseolus vulgaris* plants in the 2-leaf stage were sprayed with the spray liquid until dripping wet. After 24 hours, 2 small pieces of agar covered with *Botrytis cinerea* were placed on each leaf. The inoculated plants were placed in a darkened, moist chamber at 20° C. 3 days after the inoculation, the size of the infected spots on the leaves was rated.

The ratings were converted to percent infection. 0% denoted no infection and 100% denoted that the plants were completely infected.

In this test, the compound (1) showed a good action which was superior to that of the known compound tetramethylthiuram disulphide.

It will be appreciated that the instant specification and examples are set forth by way of illustration and not limitation, and that various modifications and changes may be made without departing from the spirit and scope of the present invention.

We claim:

1. A spiro derivative of 3-(3,5-dihalogenophenyl)-oxazolidine-2-thion-4-one of the formula

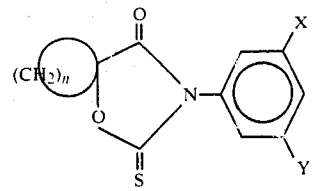

in which
X and Y each independently is halogen, and
n is 2 or 3.

2. A compound according to claim 1, wherein such compound is 1-oxa-3-aza-spiro[4,2]-hepta-3-(3,5-dichlorophenyl)-2-thion-4-one of the formula

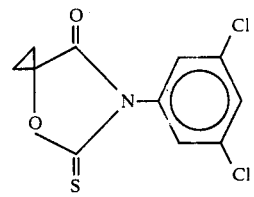

3. A compound according to claim 1, wherein such compound is 1-oxa-3-aza-spiro[4,3]-octa-3-(3,5-dichlorophenyl)-2-thion-4-one of the formula

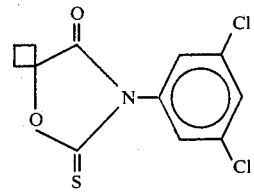

4. A compound according to claim 1, wherein such compound is 1-oxa-3-aza-spiro[4,2]-hepta-3-(3,5-dibromophenyl)-1-thion-4-one of the formula

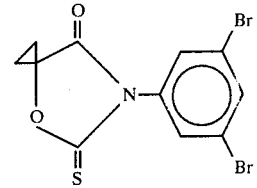

5. A compound according to claim 1, wherein such compound is 1-oxa-3-aza-spiro[4,3]-octa-3-(3,5-dibromophenyl)-2-thion-4-one of the formula

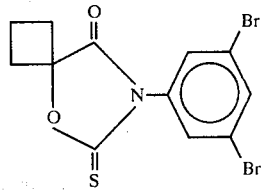

6. A compound according to claim 1, wherein such compound is 1-oxa-3-aza-spiro[4,2]-hepta-3-(3,5-diiodo-phenyl)-2-thion-4-one of the formula 7. A compound according to claim 1, wherein such compound is 1-oxa-3-aza-spiro[4,2]-hepta-3-(3-bromo-5-chloro-phenyl)-2-thion-4-one of the formula 8. A compound according to claim 1, wherein such compound is 1-oxa-3-aza-spiro[4,3]-octa-3-(3-bromo-5-chloro-phenyl)-2-thion-4-one of the formula 9. A process for the preparation of a spiro derivative of 3-(3,5-dihalogenophenyl)-oxazolidine-2-thion-4-one according to claim 1, comprising reacting an α-hydroxy-cycloalkylcarboxylic acid or acid ester of the formula in which
R is hydrogen or alkyl with 1 to 4 carbon atoms,
(a) with an isothiocyanate of the formula or
(b) with an aniline of the formula in the presence of a diluent, and then cyclizing the α-hydroxy-cycloalkyl-carboxylic acid amide formed of the formula 10. A process according to claim 9, wherein the reaction is effected at about 20° to 100° C.

11. A process according to claim 9, wherein an aromatic hydrocarbon or a halogenated hydrocarbon is used as a solvent in the reaction.

12. A process according to claim 9, wherein the reaction is effected in the presence of a tertiary amine or an alcoholate.

13. A fungicidal composition containing as active ingredient a fungicidally effective amount of a compound according to claim 1, in admixture with a diluent.

14. A method of combating fungi which comprises applying to the fungi, or to a habitat thereof, a fungicidally effective amount of a compound according to claim 1.

15. A method according to claim 14, in which said compound is
1-oxa-3-aza-spiro 4,2-hepta-3-(3,5-dichlorophenyl)-2-thion-4-one,
1-oxa-3-aza-spiro 4,3-octa-3-(3,5-dichlorophenyl)-2-thion-4-one,
1-oxa-3-aza-spiro 4,2-hepta-3-(3,-dibromophenyl)-2-thion-4-one,
1-oxa-3-aza-spiro 4,3-octa-3-(3,5-dibromophenyl)-2-thion-4-one,
1-oxa-3-aza-spiro 4,2-hepta-3-(3,5-diiodophenyl)-2-thion-4-one,
1-oxa-3-aza-spiro 4,2-hepta-3-(3-bromo-5-chlorophenyl)-2-thion-4-one or
1-oxa-3-aza-spiro 4,3-octa-3-(3-bromo-5-chlorophenyl)-2-thion-4-one.

* * * * *